(12) United States Patent
Stepanov et al.

(10) Patent No.: US 8,916,376 B2
(45) Date of Patent: Dec. 23, 2014

(54) METAL-BINDING PEPTIDES

(75) Inventors: Victor G. Stepanov, Houston, TX (US); Yamei Liu, Houston, TX (US); George E. Fox, Manvel, TX (US); George W. Jackson, Pearland, TX (US); Roger J. McNichols, Pearland, TX (US)

(73) Assignee: BioTex, Inc., Houston, TX (US)

( * ) Notice: Subject to any disclaimer, the term of this patent is extended or adjusted under 35 U.S.C. 154(b) by 1109 days.

(21) Appl. No.: 12/121,658

(22) Filed: May 15, 2008

(65) Prior Publication Data

US 2012/0165225 A1 Jun. 28, 2012

Related U.S. Application Data

(63) Continuation-in-part of application No. 12/044,737, filed on Mar. 7, 2008, now abandoned.

(60) Provisional application No. 60/917,961, filed on May 15, 2007.

(51) Int. Cl.
*C12N 15/63* (2006.01)
*C12N 15/10* (2006.01)

(52) U.S. Cl.
CPC .................... *C12N 15/1048* (2013.01)
USPC ....................................................... 435/320.1

(58) Field of Classification Search
CPC ........... C12Q 2525/205; C12Q 1/6837; C12N 15/1048; C40B 50/18; C40B 60/14; C07K 1/22; G01N 33/18; G01N 33/1813
See application file for complete search history.

(56) References Cited

U.S. PATENT DOCUMENTS

| 5,015,573 A * | 5/1991 | Yarranton et al. ........... 435/69.1 |
| 2003/0171551 A1 * | 9/2003 | Rosenblatt et al. ........ 530/388.8 |
| 2004/0242848 A1 * | 12/2004 | Owens et al. ............. 530/387.3 |

OTHER PUBLICATIONS pCT302 [online]. [Retrieved on Oct. 14, 2011]. Retrieved from the Internet: <http://openwetware.org/images/4/4f/PCT302.pdf>.*
Stepanov, et al. (2006) Stress-Driven In Vivo Selection of a Functional Mini-Gene from a RAndomized DNA Library Expressing Combinatorial Peptides in *Escherichia coli*. Molecular Biology and Evolution, v.24(7):1480-91.*
Cochran, et al. (2006) Improved Mutants from Directed Evolution are Biased to Orthologous Substitutions. Protein Engineering, Design & Selection, v.19(6):245-53.*
Tenson, et al. (1997) "Erythromycin Resistance Peptides Selected from Random Peptide Libraries," The Journal of Biological Chemistry, v.272(28):17425-30.*
Lovmar, et al. (Mar.10, 2006) The Molecular Mechanism of Peptide-mediated Erythromycin Resistance. The Jounral of Biological Chemistry, v.281(10):6742-50.*

* cited by examiner

*Primary Examiner* — Jennifer McDonald
(74) *Attorney, Agent, or Firm* — Christopher Quan

(57) ABSTRACT

The present invention is generally directed to novel functionalized biomolecules and methods for generating such biomolecules. Biomolecules may generally include nucleic acids, peptides, multicomponent molecular complexes and/or any other molecular products that may be produced by living organisms. The present invention is further directed to cells and/or organisms manipulated to produce such functionalized biomolecules. The cells contemplated by the present invention include both prokaryotic as well as eukaryotic cells. The functionalized biomolecules are produced via materials introduced into the cell using standard molecular biology techniques or are incorporated within the genomic nucleic acid of a cell by standard recombination techniques. Further contemplated is the use of such cells for sequestration of target molecules within the cells.

14 Claims, 2 Drawing Sheets

METAL-BINDING PEPTIDES

CROSS-REFERENCE TO RELATED APPLICATIONS

This application claims the benefit of U.S. provisional patent application Ser. No. 60/917,961, filed May 15, 2007, entitled "STRESS-DRIVEN IN VIVO SELECTION OF RNAs WITH USEFUL PROPERTIES", the entire contents of which are hereby incorporated by reference. This application is a continuation-in-part of U.S. utility patent application Ser. No. 12/044,737, filed Mar. 7, 2008, entitled "FUNCTIONAL NUCLEIC ACIDS FOR BIOLOGICAL SEQUESTRATION", the entire contents of which are hereby incorporated by reference.

SEQUENCE LISTING

Peptide sequences and nucleic acid sequences are provided in the sequence listing in the ASCII text file entitled "PSEQ1_P1018US01_ST25.txt", created May 13, 2014, of 4 kilobytes in size, which is hereby incorporated by reference in its entirety.

BACKGROUND OF THE INVENTION

Directed evolution of natural microbial populations has been shown to be an efficient approach to study molecular mechanisms of natural selection, adaptation and speciation. The short generation time, large population size, simple life cycle, and ease of maintenance and storage make bacterial and viral systems exceedingly suitable for evolution experiments. Nevertheless, such experiments typically require multiple iterations of the mutation-selection cycle that implies (1) diversification of parental genetic material by spontaneous or induced mutagenesis, and (2) selective amplification of successful genotypes through differential reproduction of the microorganisms under defined environmental constraints. At the end of the procedure, the acquired genetic changes can be examined and related to those phenotypic features, which differentiate the evolved cell lineages from the ancestral strain.

A simple way to direct the evolution of a microbial population is to make it propagate under an appropriately applied stress. Stress-induced imbalances in cellular metabolism result in reduced fitness of the wild type lineage. At the same time, some of the emerging mutants may exhibit a substantial tolerance of the harmful factor. During prolonged cultivation under stressful conditions, these resistant phenotypes will gradually substitute the wild type. Accordingly, the population will drift towards higher frequencies of the mutated genes associated with the resistant clones. The original genotype will eventually be replaced with a new one, which confers an improved fitness on the microbes exposed to the hostile environment.

SUMMARY OF THE INVENTION

The present invention is generally directed to novel functionalized biomolecules and methods for generating such biomolecules. Biomolecules may generally include nucleic acids, peptides, multicomponent molecular complexes and/or any other molecular products that may be produced by living organisms. The present invention is further directed to cells and/or organisms manipulated to produce such functionalized biomolecules. The cells contemplated by the present invention include both prokaryotic as well as eukaryotic cells. The functionalized biomolecules are produced via materials introduced into the cell using standard molecular biology techniques or are incorporated within the genomic nucleic acid of a cell by standard recombination techniques. Further contemplated is the use of such cells for sequestration of target molecules within the cells.

Provided herein are embodiments of an expression vector comprising a chimeric gene encoding selective biomolecule ligands capable of binding to or altering target molecules, operatively linked to a functional promoter, where the vector when transfected in a host transcribes the chimeric gene.

Also, disclosed are embodiments of an isolated cell comprising the expression vector described supra.

Additionally, disclosed are embodiments of an isolated cell comprising at least one nucleic acid sequence, incorporated into a genomic nucleic acid, where the nucleic acid encodes a biomolecule that binds to or catalytically alters a target molecule.

Also provided herein are methods for sequestering within a cell a plurality of target molecules, present in a bulk volume comprising, generating a library of nucleic acid sequences coding for biomolecules capable of binding to said target molecules; incorporating the nucleic acid sequences in at least one nucleic acid within a cell; culturing the cell to achieve a cell population; contacting the cell population with the bulk volume; and separating the cell population from the bulk volume. Furthermore, provided are methods for bioremediation of contaminants present in a bulk volume further comprising, generating a library of biomolecule ligands capable of binding to and/or altering target molecules.

Other objects, features, and advantages of the present invention will be apparent to one of skill in the art from the following detailed description and figures.

The present invention together with the above and other advantages may best be understood from the following detailed description of the embodiments of the invention illustrated in the drawings.

DETAILED DESCRIPTION OF THE INVENTION

Figure 1:
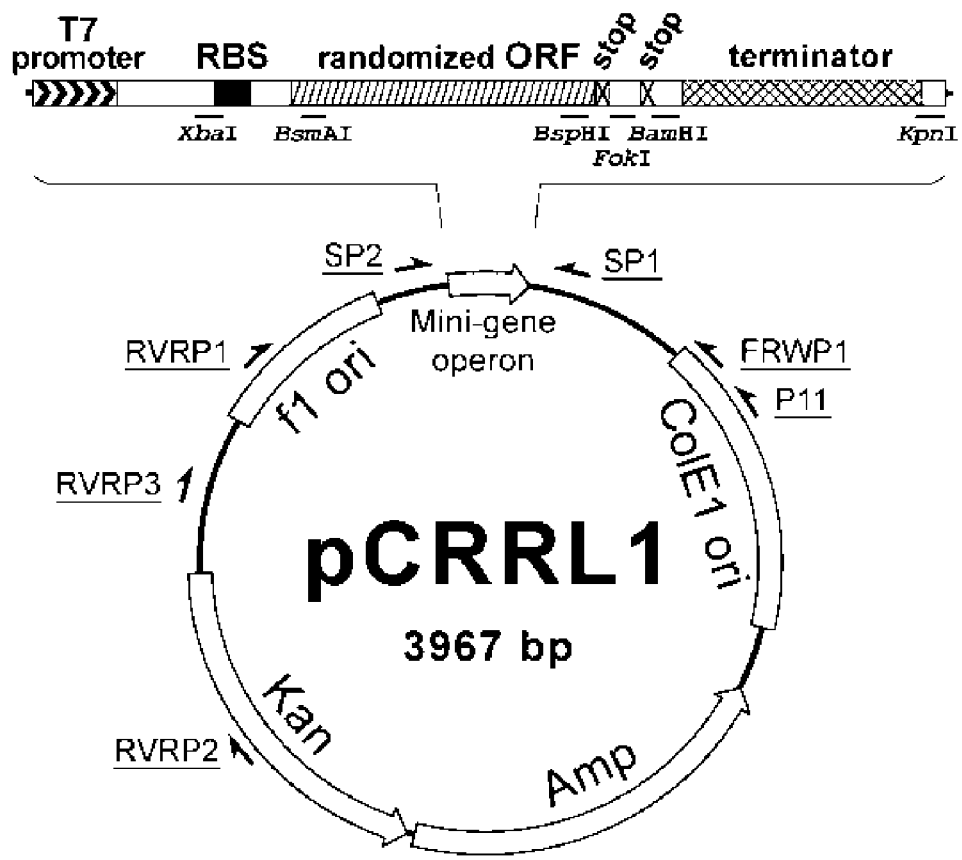
FIG. 1 illustrates an example of an expression vector of the present invention with a sequence given in SEQ ID NO 6.

The detailed description set forth below is intended as a description of the presently exemplified device provided in accordance with aspects of the present invention and is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

"Biomolecule" refers generally to molecules of biological origin, such as, for example, nucleic acids, peptides, combinations and complexes thereof, and/or other appropriate biologically generated molecules. Biomolecule may also refer to the both an expression vector encoding a functional product and the functional product itself.

An "aptamer" refers to a biomolecule that is capable of binding to a particular molecule of interest with high affinity and specificity. The binding of a ligand to an aptamer, which may be a nucleic acid such as RNA or DNA, or a combination thereof, or a peptide sequence, may also change the conformation of the aptamer. This type of interaction, with a small molecule metabolite, for example, coupled with subsequent changes in aptamer function where the aptamer is RNA, has been referred to as a 'riboswitch'. Aptamers may also comprise non-natural nucleotides, nucleotide analogs, non-natural amino acids and/or amino acid analogs. The method of selection may be by, but is not limited to, affinity chromatography and the method of amplification by reverse transcription (RT), polymerase chain reaction (PCR) and/or any other appropriate amplification method.

Aptamers have specific binding regions which are capable of forming complexes with an intended target molecule in an environment wherein other substances in the same environment are not complexed to the aptamer. The specificity of the binding is defined in terms of the comparative dissociation constants (Kd) of the aptamer for its ligand as compared to the dissociation constant of the aptamer for other materials in the environment or unrelated molecules in general. Typically, the Kd for the aptamer with respect to its ligand will be at least about 10-fold less than the Kd for the aptamer with unrelated material or accompanying material in the environment. Even more preferably, the Kd will be at least about 50-fold less, more preferably at least about 100-fold less, and most preferably at least about 200-fold less.

A nucleic acid aptamer will typically be between about 10 and about 300 nucleotides in length. More commonly, an aptamer will be between about 30 and about 100 nucleotides in length. A peptide aptamer will typically be between 10 and about 100 amino acid residues in length and more typically between 10 and 30.

The terms "nucleic acid molecule" and "polynucleotide" refer to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Cassol et al. (1992); Rossolini et al., Mol. Cell. Probes 8:91-98 (1994)). Also included are molecules having naturally occurring phosphodiester linkages as well as those having non-naturally occurring linkages, e.g., for stabilization purposes. The nucleic acid may be in any physical form, e.g., linear, circular, or supercoiled. The term nucleic acid is used interchangeably with oligonucleotide, gene, cDNA, and mRNA encoded by a gene.

A riboswitch is typically considered a part of an mRNA molecule that can directly bind a small target molecule, and whose binding of the target affects the gene's activity [Tucker B J, Breaker R R (2005). "Riboswitches as versatile gene control elements". Curr Opin Struct Biol 15 (3): 342-8]. Thus, an mRNA that contains a riboswitch is directly involved in regulating its own activity, depending on the presence or absence of its target molecule. By definition, then, a riboswitch has a region of aptamer-like affinity for a separate molecule. Thus, in the broader context of the instant invention, any aptamer included within a non-coding nucleic acid could be used for sequestration of molecules from bulk volumes. Downstream reporting of the event via "(ribo)switch" activity may be especially advantageous. A similar concept is coined by the phrase "aptazyme" in which an aptamer region is used as an allosteric control element and coupled to a region of catalytic RNA (a "ribozyme" as described below).

A ribozyme (from ribonucleic acid enzyme, also called RNA enzyme or catalytic RNA) is a RNA molecule that catalyzes a chemical reaction. Many natural ribozymes catalyze either the hydrolysis of one of their own phosphodiester bonds, or the hydrolysis of bonds in other RNAs, but they have also been found to catalyze the aminotransferase activity of the ribosome. More recently it has been shown that catalytic RNAs can be "evolved" by in vitro methods [1. Agresti J J, Kelly B T, Jäschke A, Griffiths A D: Selection of ribozymes that catalyse multiple-turnover Diels-Alder cycloadditions by using in vitro compartmentalization. Proc Natl Acad Sci USA 2005, 102:16170-16175; 2. Sooter L J, Riedel T, Davidson E A, Levy M, Cox J C, Ellington A D: Toward automated nucleic acid enzyme selection. Biological Chemistry 2001, 382(9):1327-1334.]. Winkler et al. have shown [Winkler W C, Nahvi A, Roth A, Collins J A, Breaker R R: Control of gene expression by a natural metabolite-responsive ribozyme. Nature 2004, 428:281-286.] that, similar to riboswitch activity discussed above, ribozymes and their reaction products can regulate gene expression. In the context of the instant invention, it may be particularly advantageous to place a catalytic RNA or ribozyme within a larger non-coding RNA such that the ribozyme is present at many copies within the cell for the purposes of chemical transformation of a molecule from a bulk volume. Furthermore, encoding both aptamers and ribozymes in the same non-coding RNA may be particularly advantageous.

The term "gene" is used broadly to refer to any segment of DNA associated with a biological function. Thus, genes include coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "bases" refers to both the deoxyribonucleic and ribonucleic acids. The following abbreviations are used, "A" refers to adenine as well as to its deoxyribose derivative, "T" refers to thymine "U" refers to uridine, "G" refers to guanine as well as its deoxyribose derivative, "C" refers to cytosine as well as its deoxyribose derivative. A person having ordinary skill in this art would readily recognize that these bases may be modified or derivatized to optimize the methods of the present invention.

As used herein, the term "amino acids" refers to the 20 naturally occurring amino acids used in peptide synthesis and the residues thereof when present in a peptide molecule. A person having ordinary skill in this art would readily recognize that these amino acids may be modified, derivatized and/or supplemented by artificial amino acids or analogs thereof to optimize the methods of the present invention.

Amino acids may be abbreviated as follows: A is alanine, R is arginine, N is asparagine, D is aspartic acid, C is cysteine, E is glutamic acid, Q is glutamine, G is glycine, H is histidine, I is isoleucine, L is leucine, K is lysine, M is methionine, F is phenylalanine, P is proline, S is Serine, T is threonine, W is tryptophan, Y is tyrosine, and V is valine.

The present invention is generally directed to novel functionalized biomolecules and methods for generating such biomolecules. Biomolecules may generally include nucleic acids, peptides, multicomponent molecular complexes and/or any other molecular products that may be produced by living organisms. The present invention is further directed to cells and/or organisms manipulated to produce such functionalized biomolecules. The cells contemplated by the present invention include both prokaryotic as well as eukaryotic cells. The functionalized biomolecules are produced via materials introduced into the cell using standard molecular biology techniques or are incorporated within the genomic nucleic acid of a cell by standard recombination techniques. Further contemplated is the use of such cells and biomolecules, such as for sequestration of target molecules within the cells.

In one aspect, the present invention includes a method of generating selective biomolecule ligands in vivo. In one embodiment, a library of diverse nucleic acid sequences is utilized in vivo for the selection of functionalized biomolecules. The library of nucleic acid sequences may be contained in an expression vector or vectors, each comprising a chimeric gene encoding selective biomolecule ligands capable of binding to or altering target molecules, operatively linked to a functional promoter, where the vector when transfected and/or otherwise introduced into a host organism or cell transcribes the chimeric gene. The chimeric gene may generally code for a nucleic acid sequence which may be transcribed into RNA. The transcribed RNA may be the product biomolecule ligand of the expression vector and/or it may be a functional messenger RNA (mRNA) which may subsequently bind to a ribosome where it may be translated into a peptide, which may be the product biomolecule ligand. In general, the method may comprise the steps of:
1) Building populations of a host cell or organism carrying a replicate of the expression vector;
2) Culturing said host populations under specific conditions which may include selective stress, such as, for example, the presence of a target molecule;
3) Assessing the clones which display increased resistance to said specific condition;

The method may further comprise determining the specific sequence of the expression vector after culturing and assessment as well as determination of the functional activity of the biomolecule product of the expression vector.

The chimeric gene generally includes a randomized, partially randomized and/or selected sequence which may be evaluated for functional activity in a host organism or cell. The chimeric gene may also be subject to modifications and/or mutations after the determination of the original sequence. The expression vector also generally includes a promoter having high transcriptional activity such that the chimeric gene is expressed at a high level in the host. The promoter may also include functional elements such as inducible activity. In some exemplary embodiments, the promoter is a T7 RNA polymerase promoter or a ribosomal RNA (rRNA) promoter.

In some embodiments, the expression vector includes a chimeric gene that encodes for and, when introduced into a host organism or cell, transcribes mRNA and/or mRNAs. The mRNA may typically contain at least one open reading frame (ORF) which may translate a peptide sequence when associated with a ribosome. The ORF may generally be free of unintentional interrupting stop codons, however stop codons may be utilized to selectively interrupt translation. At least a portion of the ORF is a randomized, partially randomized and/or selected sequence and may have no obvious bias for a specific function, or it may be selected for a known function. The encoded peptide may generally be a peptide aptamer which may be selected for specific functional activity against a target molecule, such as, for example, binding to or modifying a target molecule. Target molecules contemplated include, but are not limited to, metal ions, organic molecules, viral particles, biological molecules, such as antibodies, proteins, enzymes, pharmaceuticals and/or any other substance to be removed and/or treated from a bulk volume. In particular, wastes and contaminants are contemplated. Sequestration of target molecules refers to binding to or altering the target molecules.

Bulk volumes can be treated with the genetically modified cells containing functional aptamer. The aptamer may be a peptide aptamer or a nucleic acid aptamer. Further embodiments and methods for nucleic acids are disclosed in detail in U.S. utility patent application Ser. No. 12/044,737, filed Mar. 7, 2008, entitled "FUNCTIONAL NUCLEIC ACIDS FOR BIOLOGICAL SEQUESTRATION", the entire contents of which are hereby incorporated by reference. The genetically modified cells may treat, remove and/or sequester target molecules in the bulk volume. The presence of a high concentration of binding and/or catalytic biomolecules inside the cell creates an equilibrium shift in the bulk volume whereby a given substance is removed from the bulk volume and sequestered in the cell by binding to and/or catalytic action by the biomolecules. The sequestration and/or catalytic action generally constantly removes the targeted molecule from the equilibrium, resulting in a constant influx of the target molecule into the cell. The genetically modified cells, harboring the sequestered target molecules, are then removed from the bulk volume. Appropriate methods of removal of the genetically modified cells include, but are not limited to, filtration, sedimentation, centrifugation (accelerated sedimentation), flocculation, adsorption, membrane filtration, biofilm formation, membrane bioreactor, and/or any other physical configuration otherwise known in the art as a bioreactor, used to separate the treated waste stream from the cells.

Such bioreactors also include in situ remediation techniques in which the genetically modified cells are released into a controlled volume of the environment. Sequestration and/or chemical transformation of contaminants then occurs before the controlled volume passes into another portion of the environment. This is particularly useful in examples where the cells are introduced into waste water and/or other waste streams which are in contact with the environment. The genetically modified cells can be immobilized for contact with a bulk volume while not being distributed into the volume. Immobilization techniques include but are not limited to, microbial mats, mineral amendments, polymer gel formulations, and/or any other appropriate immobilization technique or combination may be utilized. Genetically-modified cells can be tagged for identification such that they can be isolated from a particular environment. Additionally, the cells can be genetically modified to include features for their removal from an environment, such as, for example, a susceptibility factor to a particular substance, an affinity to a particular separation method, and/or any other appropriate removal method.

Further, the cells may also include features for increasing the sequestration rate of a substance in a bulk volume. For example, a molecular channel and/or transporter may be utilized to enhance transport of a substance across the cell membrane into the cell. Metal ion and/or other small ion transport molecules are known and can be incorporated by genetic modification of the cell. Additionally, the cells can be engineered to export the biomolecules into bulk environment, for example, by including nucleic acid sequences encoding viral packaging and/or export signals. Reuptake of biomolecule bound to the target molecule can be engineered for example, by binding to cell surface receptors and/or any other appropriate method.

Biomolecules as discussed above can be utilized as affinity handles for purification. For example, biomolecule handle may be attached to a molecule of therapeutic or diagnostic value, such as a peptide aptamer affinity handle coupled to an antibody. The desired high-value molecule is readily purified by binding the aptamer portion. Aptamers to common chromatographic matrices such as agarose, Sephadex, Sepharose, as well as more specialized affinity resins with immobilized metals, antibodies, proteins, peptides, and/or any other appropriate affinity material can be utilized. Aptamers to such affinity ligands are developed by well established in vitro methods or by in vivo methods similar to those discussed above. Inserted aptamers fused to desired molecules can be used for therapeutic and/or diagnostic functions, such as, for example, antibodies, hormones, signaling proteins, enzymes and/or any other appropriate molecule. Aptamers utilized as affinity handles for molecules can be sequenced, probed by hybridization, and/or characterized by some other analytical technique, such as, for example, sequencing or mass spectrometry for organism identification. In some embodiments, the aptamer itself may be a desired molecule which may be purified by affinity to its target molecule.

Inserted functional biomolecules are also useful for highly specific intracellular labeling and/or cellular signal tracking. For example, an aptamer including a fluorescent- and/or radio-label can be concatenated and/or fused to an aptamer targeting a particular cellular component, such as an important protein, enzyme, organelle, and/or any other appropriate component. This aptamer fusion can be expressed at high levels in a cell. Cells expressing such aptamers may thus have a built-in ability to monitor specific cellular processes.

In yet another embodiment, there is provided a method for sequestering within a cell a plurality of target molecules, present in a bulk volume comprising, generating a library of nucleic acid sequences coding for functional biomolecules binding to the target molecules; incorporating the nucleic acid sequences into a cell; culturing the cell to achieve a cell population; Contacting the cell population with the bulk volume; and separating the cell population from the bulk volume. The method further comprises recovering the target molecule from the cell population. In general, the target molecules are inorganic molecules, organic molecules, toxins, proteins, peptides, and viral particles. In a related embodiment, the target molecules are hormones, antibodies, proteins, enzymes, pharmaceuticals or valuable metals. In general, the separation is accomplished by a method selected from the group consisting of filtration, sedimentation, flocculation, adsorption, membrane filtration, biofilm formation and membrane bioreactor interaction.

The following examples are given for the purpose of illustrating various embodiments of the invention and are not meant to limit the present invention in any fashion.

Example of Nucleic Acid Library Construction

A mini-gene library, as shown in FIG. 1, was designed to express a 20-mer peptide with 12 randomized positions in its central part and an invariant four amino acid-long N- and C-terminus. The core element of the library was a 100-bp dsDNA cassette, which was developed as a standard module for composite genetic constructs with randomized segments. The cassette contained a 60-bp ORF with a Shine-Dalgarno sequence located 8 bp upstream of the translation start codon, XbaI and BamHI restriction sites at the ends, and several auxiliary restriction sites (BsmAI, FokI, and BspHI) that were intended for cassette modification and not used in this study. Randomized segment of the ORF was presented as eleven contiguous NNC triplets followed by one SRC triplet on the non-coding DNA strand, where N corresponds to A, T, G, or C, S is G or C, and R is A or G. The SRC triplet together with downstream invariant triplets encoded a five amino acid-long C-terminal tag (H/R/D/G)SAHE, which was expected to increase peptide stability in the E. coli cytoplasm. The total sequence space of the library theoretically included $7.04 \times 10^{13}$ DNA variants, or $3.45 \times 10^{13}$ peptide variants. The use of randomized triplets with a fixed C in the third position inhibits the emergence of internal stop-codons, equalizes distribution of different amino acids in the peptide sequence, and significantly decreases the coding redundancy of the library. It also diminishes the risk of a bias caused by an occasional digestion of the randomized segment by restriction enzymes in the course of library construction. On the other hand, this design excludes methionine, tryptophan, lysine, glutamine and glutamic acid from the variable part of the peptide. However, since none of the above-mentioned amino acids possesses a unique functionality that cannot be provided by other amino acids, they were considered to be dispensable in this example. The cassette was inserted unidirectionally into pCR21-T7pt vector between a T7 promoter and transcription terminator. This resulted in a plasmid library designated as pCRRL1, which carries ampicillin and kanamycin resistance determinants and requires host-provided T7 RNA polymerase to express the randomized ORF. Placing the randomized ORF under strong promoter on high copy number plasmid ensures a very intense intracellular synthesis of the 20-mer peptide and therefore was expected to contribute significantly to the modified E. coli phenotype. It is noted that strong expression of the mini-gene might be a source of metabolic stress, which would combine with the imposed environmental one. However, when concentration of a bacteriotoxic substance in the medium is close to lethal, the environmental stress is likely to prevail and thus to direct the competition between clonal lineages associated with different mini-gene variants.

The pCR21-T7pt plasmid was derived from cloning vector pCR2.1 (Invitrogen) by rearrangement of its MCS sequence and introduction of the T7 late terminator, TΦ, downstream of the T7 RNA polymerase promoter and MCS. The plasmid was cleaved at XbaI and BamHI sites, treated with calf alkaline phosphatase, and gel purified. A 100 bp-long DNA cassette harbouring an ORF with randomized sequence was synthesized in a single reaction by overlap extension PCR from three deoxyoligonucleotides, 32-mer SEQ ID NO 3: d(GCTCTAGAAGGAGATATACATATGTCTCACGC), 32-mer SEQ ID NO 4: d(CGGGATCCTAGGGATGTTATTCATGAGCGGAG), and 61-mer SEQ ID NO 5: d(CATATGTCTCACGCT(NNC)11SRCTCCGCTCATG), where N is an equimolar mixture of A, T, G, or C, S is an equimolar mixture of G or C, and R is an equimolar mixture of A or G. The PCR product was treated with XbaI and BamHI restriction enzymes, gel purified, and ligated into linearised dephosphorylated pCR21-T7pt plasmid (40 Units/µl of T4 DNA ligase, 0.04 Unit/µl of yeast inorganic pyrophosphatase in 1×NEB T4 DNA ligase buffer, 100 hrs at 8-12° C.). The resulting plasmid library, pCRRL1 (FIG. 1), was further purified by phenol-chloroform extraction and ethanol precipitation. The size of the inserted DNA fragment was verified by PCR with a pair of flanking primers, SP1 and SP2 (see above).

No cassette oligomerization or unproductive re-circulization of pCR21-T7pt was observed.

Example of Selection and Primary Characterization

Figure 2:
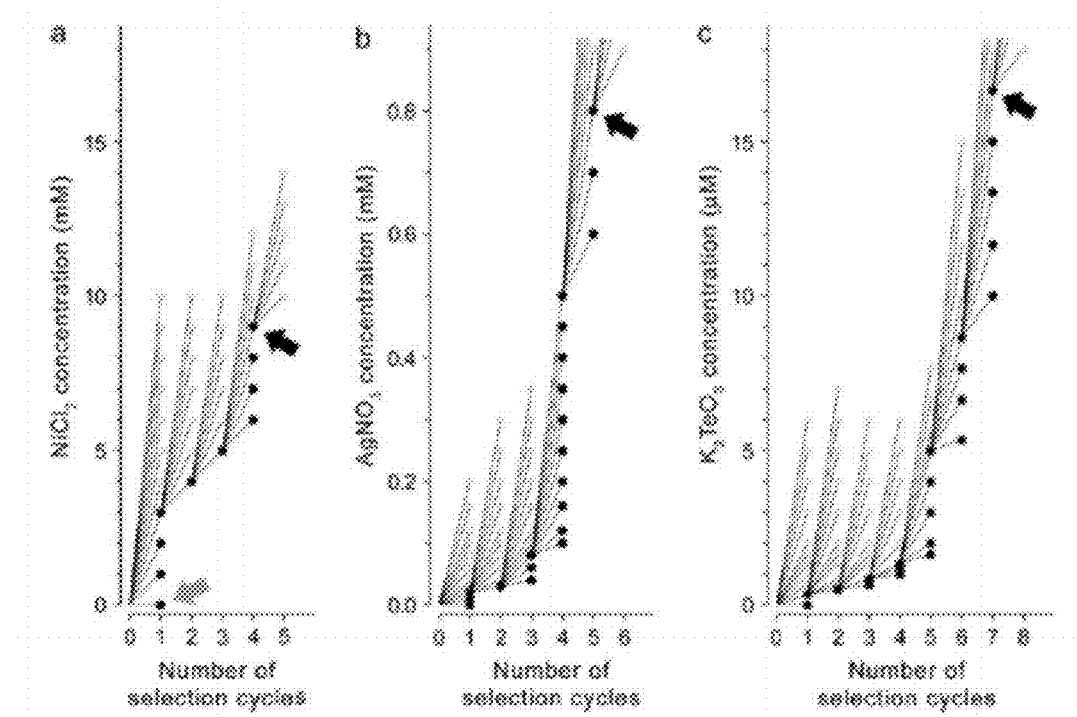
FIG. 2 illustrates the selection of cultures resistant to selected stresses.
Figure 2A:
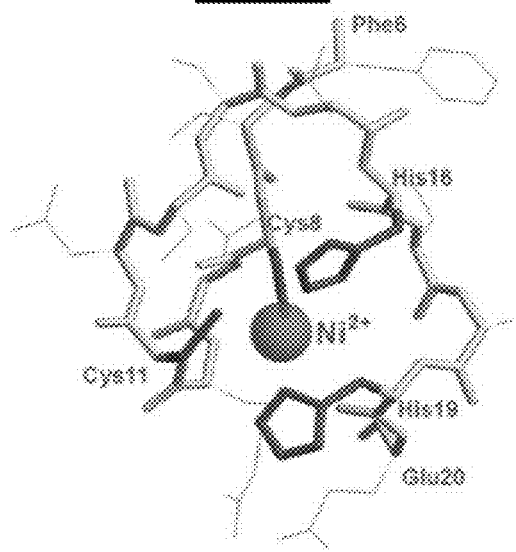
FIG. 2a shows a hypothetical model of a peptide of the present invention.

The pCRRL1 library was transformed into *E. coli* BLR (DE3) cells, which carry a T7 RNA polymerase gene under control of IPTG-regulated lacUV5 promoter. The number of individual clones was estimated to be ~$10^5$. The clone library was allowed to grow for 4 hrs in order to obtain several replicates of it, and then split into parts intended for parallel evolution experiments using different toxic agents. Expression of the randomized ORF was induced by IPTG, and the multi-step selection experiment was started by adding appropriate amounts of $NiCl_2$, $AgNO_3$, or $K_2TeO_3$ to the cell cultures, as shown in FIG. 2 with the selection of the *E. coli* clones resistant to $NiCl_2$ (a), $AgNO_3$ (b), and $K_2TeO_3$ (c). Large filled circles represent bacterial cultures successfully growing at indicated concentrations of each toxic agent. Small open circles mark the conditions under which the bacterial cultures did not exhibit noticeable growth during a 24 hours selection cycle. Since no bacterial growth was observed at $AgNO_3$ concentrations above 0.9 mM and $K_2TeO_3$ concentrations above 18 mM, the corresponding data points are not shown on plates (b) and (c), respectively. Black arrows point to the most resistant bacterial cultures, from which individual clones have been isolated for further studies of their toxicity tolerance. Grey arrow marks the culture, which was used as a non-adapted control in tests of the bacterial resistance towards nickel, silver, and tellurite. After 22-24 hrs of growth under stress, bacterial cultures exhibiting the highest toxicity tolerance in each set were used as a seed for the next cycle. A concentration gradient of the toxic agents was chosen to cover a range within which an MIC was expected to be found. Thus, at every step the selective pressure was adjusted depending on the achieved level of the toxicity tolerance to keep the evolving bacterial populations under subinhibitory conditions. Substantial increase in bacterial resistance to $Ni^{2+}$, $Ag^+$, and $TeO_3^{2-}$ was observed during four, five, and seven consecutive selection cycles, respectively. After that, no further change in toxicity tolerance was detected. During the selection procedure, the apparent MIC values increased from 4 to 10 mM $NiCl_2$, from 0.03 to 0.90 mM $AgNO_3$, and from 0.7 to 20 μM $K_2TeO_3$. Eight clones were isolated from each of the three evolved resistant populations by plating. These were tested for the dependence of growth on mini-gene expression by measuring OD600 after 24 hrs of cultivation in the presence of corresponding toxic agent, with and without IPTG. Significant IPTG-induced growth improvement was observed for several $Ni^{2+}$-resistant clones while growth of $Ag^+$- and $TeO_3^{2-}$-resistant selectants was not affected by IPTG. Plasmid sequencing revealed absolute sequence homogeneity within each group of the studied clones. All eight $Ni^{2+}$-resistant clones harbored the same plasmid (designated as pCRRL1-N94-01) with a mini-gene variant coding for the peptide MSHAYFVCNRCDSSNHSAHE (SEQ ID NO 1), a structural model of which is shown in FIG. 2a. In addition, a 9-bp deletion was detected in the spacer region between the ORF and the transcription terminator. However, since no important element of the mini-gene operon was located there, the deletion was unlikely to affect the peptide expression. $Ag^+$-resistant clones were found to bear pCRRL1-A226-01 plasmid with mini-gene variant coding for an 18-mer with the sequence MSHATATPASRRRLPLRS (SEQ ID NO 2). The shortening of the peptide was due to two non-contiguous single-base deletions inside the ORF, which resulted in frameshift and premature translation stop. Interestingly, the first nucleotide in the transcribed part of the mini-gene operon was found to be T instead of the original G. This can decrease the transcription efficiency and disrupt a stability tag at the 5'-terminus of the transcript, thus making it vulnerable to ribonucleolytic degradation. All $TeO_3^{2-}$-resistant clones carried a version of plasmid pCRRL1-T507-01 that has a 225-bp deletion of the whole mini-gene transcriptional unit together with adjacent downstream sequence. This deletion obviously abolishes T7 RNA polymerase activity on the plasmid, making it irresponsive to IPTG induction.

Example of Assessment of Mini-Gene Dependent Toxicity Tolerance

The existence of a positive correlation between the level of mini-gene expression and the extent of toxicity tolerance would strongly argue in favor of a role for the mini-gene in the mechanism of stress resistance of the evolved clones. Therefore, IPTG dependence of the toxicity tolerance was explored to establish the importance of the selected mini-gene variants for the improved bacterial performance under stress. Comparison of the bacterial growth parameters measured in the presence and absence of IPTG made it possible to distinguish the specific effect of mini-gene expression on culture survival and propagation from the basal resistance to the hostile environment acquired through adaptive genomic mutations. In the case of $TeO_3^{2-}$-resistant clones, the observed lack of IPTG influence on their growth coincides with the deletion of the mini-gene operon from the plasmid. Thus, it is evident that the evolved $TeO_3^{2-}$ tolerance must be wholly attributed to mutations in the bacterial chromosome. The situation with the $Ag^+$-resistant selectants is less certain. The presence of a seemingly functional mini-gene operon in the plasmid was nevertheless not accompanied by an IPTG-induced stimulation of bacterial growth in $Ag^+$-containing medium. For three of the selected clones, the effect of IPTG on the growth curves was studied more thoroughly at 0.02-0.8 mM $AgNO_3$ to confirm the results of the initial tests. Within the accuracy of measurement no difference was found between cultures grown in the presence and absence of IPTG. Transformation of the original *E. coli* BLR(DE3) strain with plasmids isolated from the resistant clones did not result in a phenotype with increased silver tolerance. Therefore, it was concluded that either the peptide expressed from the mini-gene does not contribute by itself to the evolved silver tolerance, or the expression proceeds with very low efficiency. Among eight tested $Ni^{2+}$-resistant selectants, four exhibited two- to four-fold IPTG-induced increase in $OD_{600}$ measured after 24 hrs of cultivation in 9 mM $NiCl_2$-containing medium. For the rest of the clones, only marginal growth stimulation by IPTG was observed under the same conditions. To elucidate such a diverse behavior, two clones representing the extremities of bacterial response to IPTG, N9405 and N9408, were taken for a detailed study of IPTG influence on their growth under nickel stress. It was found that IPTG significantly stimulates the growth of both clones when the concentration of $NiCl_2$ in the medium was 4 mM and above. At lower nickel concentrations, IPTG provided little stimulation, or even inhibited bacterial growth. Despite generally similar reaction to the IPTG induction, the clones apparently differed in their growth parameters, especially in the duration of the lag phase. It was concluded that the mini-gene is active in both selectants but its actual contribution to the evolved nickel tolerance is likely to be modulated by differences in genetic background and may not be obvious under some experimental conditions. In contrast to the resistant clones, the non-adapted control culture was able to grow only when $NiCl_2$ concentration in the medium was below 4 mM, and was always insensitive to IPTG induction. Since the basal nickel tolerance of N9405 and N9408 clones was significantly higher than that of the control culture, it is clear that they acquired adaptive genomic mutations during the selection procedure.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes to the claims that come within the meaning and range of equivalency of the claims are to be embraced within their scope. Further, all published documents, patents, and applications mentioned herein are hereby incorporated by reference, as if presented in their entirety.

What is claimed is:

1. An expression vector comprising:
   a chimeric gene encoding a peptide, operatively linked to a functional promoter, said expression vector when inserted into a host transcribes said chimeric gene into a gene product which is translated into said peptide which is capable of binding to at least one target molecule which induces stress on said host, said peptide including an amino acid sequence selected from the group consisting of SEQ ID NO 1, MSHAYFVCNRCDSSNHSAHE and SEQ ID NO 2, MSHATATPASRRRLPLRS;
   wherein said peptide has a randomly selected peptide sequence which is not obviously biased for a specific function and is selected by sequential culturing of a host exposed to said target molecule and identifying conferred resistance to said stress on said host caused by said target molecule.

2. The expression vector of claim 1, wherein said vector further comprises at least one of a selection marker or a marker for selective induction.

3. The expression vector of claim 2, wherein said vector further comprises at least one selection marker and wherein said selection marker is an antibiotic resistance marker.

4. The expression vector of claim 1, wherein said promoter is a T7 RNA polymerase or a ribosomal RNA promoter.

5. The expression vector of claim 1, wherein said at least one target molecule is a waste fluid contaminant.

6. An isolated cell comprising said expression vector of claim 1.

7. The cell of claim 6, wherein said cell is a prokaryotic cell or a eukaryotic cell.

8. An isolated cell comprising:
   at least one artificially inserted nucleic acid sequence encoding mRNA, said mRNA encoding a peptide having a randomly selected sequence which is not obviously biased for any specific function which binds to a target molecule which induces stress on said cell, said peptide includes an amino acid sequence selected from the group consisting of SEQ ID NO 1, MSHAYFVCNRCDSSNHSAHE and SEQ ID NO 2, MSHATATPASRRRLPLRS;
   wherein said at least one nucleic acid sequence is selected by sequential culturing of cells containing said sequence with exposure to at least one target molecule and identifying conferred resistance to said stress caused by said target molecule.

9. The cell of claim 8, wherein said cell is a prokaryotic cell or a eukaryotic cell.

10. The cell of claim 8, wherein said target molecule is a waste fluid contaminant.

11. A set of isolated cells comprising:
    a plurality of cells, each of said cells comprising at least one artificially inserted nucleic acid sequence encoding mRNA;
    wherein each of said plurality of cells comprises a different artificially inserted nucleic acid sequence encoding mRNA, at least one of which encodes a peptide having a randomly selected sequence which is not obviously biased for any specific function which binds to a desired target molecule and confers an identifiable resistance to stress induced by said desired target molecule to one of said plurality of cells, said peptide includes an amino acid sequence selected from the group consisting of SEQ ID NO 1, MSHAYFVCNRCDSSNHSAHE and SEQ ID NO 2, MSHATATPASRRRLPLRS.

12. The set of isolated cells of claim 11, wherein said peptide comprises a randomly selected amino acid sequence in an open reading frame.

13. The set of isolated cells of claim 11, wherein said peptide comprises a peptide aptamer.

14. The set of isolated cells of claim 11, wherein said resistance to stress caused by said desired target molecule comprises survivability of at least one of said plurality of cells when exposed to said desired target molecule.

* * * * *

SEQUENCE LISTING

```
<160> NUMBER OF SEQ ID NOS: 6

<210> SEQ ID NO 1
<211> LENGTH: 20
<212> TYPE: PRT
<213> ORGANISM: Artificial Sequence
<220> FEATURE:
<223> OTHER INFORMATION: Artificially synthesized sequence

<400> SEQUENCE: 1

Met Ser His Ala Tyr Phe Val Cys Asn Arg Cys Asp Ser Ser Asn His
1               5                   10                  15

Ser Ala His Glu
            20

<210> SEQ ID NO 2
<211> LENGTH: 18
<212> TYPE: PRT
<213> ORGANISM: Artificial Sequence
<220> FEATURE:
<223> OTHER INFORMATION: Artificially synthesized sequence

<400> SEQUENCE: 2

Met Ser His Ala Thr Ala Thr Pro Ala Ser Arg Arg Arg Leu Pro Leu
1               5                   10                  15

Arg Ser

<210> SEQ ID NO 3
<211> LENGTH: 32
<212> TYPE: DNA
<213> ORGANISM: Artificial Sequence
<220> FEATURE:
<223> OTHER INFORMATION: Artificially synthesized sequence

<400> SEQUENCE: 3
gctctagaag gagatataca tatgtctcac gc                                     32

<210> SEQ ID NO 4
<211> LENGTH: 32
<212> TYPE: DNA
<213> ORGANISM: Artificial Sequence
<220> FEATURE:
<223> OTHER INFORMATION: Artificially synthesized sequence

<400> SEQUENCE: 4
cgggatccta gggatgttat tcatgagcgg ag                                     32

<210> SEQ ID NO 5
<211> LENGTH: 61
<212> TYPE: DNA
<213> ORGANISM: Artificial Sequence
<220> FEATURE:
<223> OTHER INFORMATION: Artificially synthesized sequence
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
```

<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t

<400> SEQUENCE: 5
catatgtctc acgctnncnn cnncnncnnc nncnncnncn ncnncnncsr ctccgctcat    60
g                                                                   61

<210> SEQ ID NO 6
<211> LENGTH: 72
<212> TYPE: DNA
<213> ORGANISM: Artificial Sequence
<220> FEATURE:
<223> OTHER INFORMATION: Artificially synthesized sequence
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)

```
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 6
atgtctcacg ctnncnncnn cnncnncnnc nncnncnncn ncnncsrctc cgctcatgaa      60
taacatccct ag                                                          72
```